US006692752B1

(12) United States Patent
Slaoui et al.

(10) Patent No.: US 6,692,752 B1
(45) Date of Patent: Feb. 17, 2004

(54) METHODS OF TREATING HUMAN FEMALES SUSCEPTIBLE TO HSV INFECTION

(75) Inventors: Moncef Mohamed Slaoui, Rixensart (BE); Pierre G. Vandepapeliere, Rixensart (BE)

(73) Assignee: SmithKline Beecham Biologicals S.A. (BE)

( * ) Notice: Subject to any disclaimer, the term of this patent is extended or adjusted under 35 U.S.C. 154(b) by 0 days.

(21) Appl. No.: 09/661,926

(22) Filed: Sep. 14, 2000

Related U.S. Application Data

(63) Continuation-in-part of application No. PCT/EP99/06623, filed on Sep. 8, 1999.

(51) Int. Cl.$^7$ ............................................. A61K 39/395
(52) U.S. Cl. ................................ 424/231.1; 424/279.1; 424/283.1; 530/826
(58) Field of Search ............................. 424/231.1, 279.1, 424/283.1; 530/826

(56) References Cited

U.S. PATENT DOCUMENTS

| | | | |
|---|---|---|---|
| 4,235,877 A | 11/1980 | Fullerton | |
| 4,372,945 A | 2/1983 | Likhite | |
| 4,474,757 A | 10/1984 | Arnon et al. | |
| 5,057,540 A | 10/1991 | Kensil et al. | |
| 6,027,730 A | * 2/2000 | Francotte et al. | ......... 424/229.1 |

FOREIGN PATENT DOCUMENTS

| | | |
|---|---|---|
| EP | 139417 | 8/1984 |
| EP | 00576478 B1 * | 1/1994 |
| EP | 0689454 | 3/1994 |
| GB | 2220211 | 1/1990 |
| WO | WO 92/03467 | 3/1992 |
| WO | WO 92/16231 | 10/1992 |
| WO | WO 93/02184 | 2/1993 |
| WO | WO 94/00152 | 1/1994 |
| WO | WO 94/00153 | 1/1994 |
| WO | WO 94/05792 | 3/1994 |
| WO | WO 94/20137 | 9/1994 |
| WO | WO 94/21292 | 9/1994 |
| WO | WO 95/17209 | 6/1995 |
| WO | WO 95/17210 | 6/1995 |
| WO | WO 96/02555 | 2/1996 |
| WO | WO 96/16231 | 5/1996 |
| WO | WO 96/19496 | 6/1996 |
| WO | WO 96/31618 | 10/1996 |
| WO | WO 96/33739 | 10/1996 |

OTHER PUBLICATIONS

Straus et al. "Placebo–controlled trial of vaccination with recombinant glycoprotein D of herpes simplex virus type 2 for immunotherapy of genital herpes", The Lancet, vol. 343 (Jun. 11, 1994), pp. 1460–1463.*

Cornellssen, et al., "The Transferrin Receptor Expressed by Gonococcal Strain FA1090 is Required for the Experimental Infection of Human Male Volunteers", *Molecular Microbiology*, 27(3): 611–616 (1998).

Washington, et al., "*Chlamydia trachomatis* Infections in the United States. What Are They Costing Us?", *JAMA*, 257(15): 2070–2072 (1987).

Grayston, et al., "New Knowledge of Chlamydiae and the Diseases They Cause", *The Journal of Infectious Diseases*, 132(1): 87–105 (1975).

Grayston, et al., "Importance of Reinfection in the Pathogenesis of Trachoma", *Reviews of Infectious Diseases*, 7(6): 717–725 (1985).

Morrison, et al., "Chlamydial Disease Pathogenesis. The 57–kD Chlamydial Hypersensitivity Antigen is a Stress Response Protein", *J. Exp. Med.*, 170: 1271–1283 (1989).

Blander, et al., "Mice Immunized with a Chlamydial Extract Have No Increase in Early Protecitve Immunity Despite Increased Inflammation Following Genital Infection by the Mouse Pneumonitis Agent of *Chlamydial trachomatis*", *Infection and Immunity*, 62(9): 3617–3624 (1994).

Wang, et al., "Immunotyping of *Chlamydia trachomatis* with Monoclonal Antibodies", *The Journal of Infectious Diseases*, 152(4): 791–800 (1985).

Bavoil, et al., "Role of Disulfide Bonding in Outer Membrane Structure and Permeability in *Chlamydia trachomatis*", *Infection and Immunity*, 44(2): 479–485 (1984).

Hatch, et al., "Synthesis of Disulfide–Bonded Outer Membrane Proteins During the Developmental Cycle of *Chlamydia psittaci* and *Chlamydia trachomatis*", *Journal of Bacteriology*, 165(2): 379–385 (1986).

Stephens, et al., "Diversity of *Chlamydia trachomatis* Major Outer Membrane Protein Genes", *Journal of Bacteriology*, 169(9): 3879–3885 (1987).

Yuan, et al., "Nucleotide and Deduced Amino Acid Sequences for the Four Variable Domains of the Major Outer Membrane Proteins of the 15 *Chlamydia trachomatis* Serovars", *Infection and Immunity*, 57: 1040–1049 (1989).

(List continued on next page.)

*Primary Examiner*—Jeffrey Stucker
(74) *Attorney, Agent, or Firm*—William R. Majarian; Steve Venetianer; Charles M. Kinzig

(57) ABSTRACT

A method of administering a vaccine to females to prevent or treat infections associated with pathogens which cause sexually transmitted diseases is described. The vaccine comprises one or more antigens for the prevention or treatment of sexually transmitted diseases, for example an HSV glycoprotein D or an immunological fragment thereof, and an adjuvant, especially a TH-1 inducing adjuvant. The use of the vaccine components for the formulation of a vaccine composition for the prevention or treatment of sexually transmitted diseases in female subjects is also described.

13 Claims, No Drawings

OTHER PUBLICATIONS

Baehr, et al., "Mapping Antigenic Domains Expressed by *Chlamydia trachomatis* Major Outer Membrane Protein Genes", *Proc. Natl. Acad. Sci. USA*, 85: 4000–4004 (1988).

Lucero, et al., "Neutralization of *Chlamydia trachomatis* Cell Culture Infection by Serovar–Specific Monoclonal Antibodies", *Infection and Immunity*, 50(2): 595–597 (1985).

Zhang, et al., "Protective Monoclonal Antibodies Recognize Epitopes Located on the Major Outer Membrane Protein of *Chlamydia trachomatis*", *The Journal of Immunology*, 138(2): 575–581 (1987).

Peterson, et al., "Protective Role of Magnesium in the Neutralization by Antibodies of *Chlamydia trachomatis* Infectivity", *Infection and Immunity*, 56(4): 885–891 (1988).

Zhang, et al., "Protective Monoclonal Antibodies to *Chlamydia trachomatis* Serovar– and Serogroup–Specific Major Outer Membrane Protein Determinants", *Infection and Immunity*, 57(2): 636–638 (1989).

Allen, et al., "A Single Peptide from the Major Outer Membrane Protein of *Chalmydia trachomatis* Elicits T Cell Help for the Production of Antibodies to Protective Determinants", *The Journal of Immunology*, 147(2): 674–679 (1991).

Su, et al., "Identification and Characterization of T Helper Cell Epitopes of the Major Outer Membrane Protein of *Chlamydia trachomatis*", *The Journal of Experimental Medicine*, 172: 203–212 (1990).

Manning, et al., Expression of the Major Outer Membrane Protein of *Chlamydia trachomatis*, *Infection and Immunity*, 61(10): 4093–4098 (1993).

Koehler, et al., "Overexpression and Surface Localization of the *Chlamydia trachmatis* Major Outer Membrane Protein in *Escherichia coli*", *Molecular Microbiology*, 6(9): 1087–1094 (1992).

Pickett, et al., "High–Level Expression and Epitope Localization of the Major Outer Membrane Protein of *Chlamydia trachomatis* Serovar L1", *Molecular Microbiology*, 2(5): 681–685 (1988).

Taylor, et al., "Oral Immunization with Chlamydial Major Outer Membrane Protein (MOMP)", *Investigative Opthalmology & Visual Science*, 29(12): 1847–1853 (1988).

Batteiger, et al., "Partial Protection Against Genital Reinfection by Immunization of Guinea–Pigs with Isolated Outer–Membrane Proteins of the Chlamydial Agent of Guinea–Pig Inclusion Conjunctivitis", *Journal of General Microbiology*, 139: 2965–2972 (1993).

Tuffrey, et al., "Heterotypic Protection of Mice Against *Chlamydial Salpingitis* and Colonization of the Lower Genital Tract with a Human Serovar F Isolate of *Chlamydia trachomatis* by Prior Immunization with Recombinant Serovar L1 Major Outer–Membrane Protein", *Journal of General Microbiology*, 138: 1707–1715 (1992).

Tuffrey, et al., "*Salpingitis* in Mice Induced by Human Strains of *Chlamydia trachomatis*", *Br. J. Exp. Path.*, 67: 605–616 (1986).

Tuffrey, et al., "Infertility in Mice Infected Genitally with a Human Strain of *Chlamydia trachomatis*", *J. Reprod. Fert.*, 78: 251–260 (1986).

Ramsey, et al., "Resolution of Chlamydial Genital Infection in B–Cell–Deficient Mice and Immunity to Reinfection", *Infection and Immunity*, 56(5): 1320–1325 (1988).

Rank, et al., "Chronic Chlamydial Genital Infection in Congenitally Athymic Nude Mice", *Infection and Immunity*, 48(3): 847–849 (1985).

Igietseme, et al., "Susceptibility to Reinfection After a Primary Chlamydial Genital Infection is Associated with a Decrease of Antigen–Specific T Cells in the Genital Tract", *Infection and Immunity*, 59(4): 1346–1351 (1991).

Igietseme, et al., "Resolution of Murine Chlamydial Genital Infection by the Adoptive Transfer of a Biovar–Specific, TH1 Lymphocyte Clone", *Regional Immunology*, 5(6): 317–324 (1993).

Igietseme, et al., "Role for CD8+ T Cells in Antichlamydial Immunity Defined by Chlamydia–Specific T–Lymphocyte Clones", *Infection and Immunity*, 62(11): 5195–5197 (1994).

Eisenberg, et al., "Comparative Structural Analysis of Glycoprotein gD of Herpes Simplex Virus Types 1 and 2", *J. Virol.*, 35: 428–435 (1980).

Cohen, et al., "Localization of Discontinuous Epitopes of Herpes Simplex Virus Glycoprotein D: Use of a Nondenaturing ("Native" Gel) System of Polyacrylamide Gel Electrophoresis Coupled with Western Blotting", *J. Virol.*, 60: 157–166 (1986).

Eing, et al., "Neutralizing Activity of Antibodies Against the Major Herpes Simplex Virus Type 1 Glycoproteins", *J. Med. Virol.*, 127: 59–65 (1989).

J. Cason, "Papillomavirus Vaccines. Current Status.", *Clin. Immunother.*, 1(4): 293–306 (1994).

M.E. Hagenesee, "Progress in the Development of HPV Vaccines", *Infections in Medicine*, 14(7): 555–556, 559–564 (1997).

Gotschlich, et al., Porin Protein of *Neisseria gonorrhoeae*: Cloning and Gene Structure. *PNAS USA*, 84(22): 8135–8139 (1987).

Smith et al., "Sequence Evolution of the porB Gene of *Neisseria gonorrhoeae* and *Neisseria meningitidis*: Evidence of Positive Darwinian Selection", *Mol. Biol. Evol.*, 12(3): 363–370 (1995).

Diena, et al., "The Lipopolysaccharide (R Type) as a Common Antigen of *Neisseria gonorrhoeae*. I. Immunizing Properties", *Can. J. Microbiol.*, 24(2): 117–123 (1978).

Brossay, et al., "Idiotype and Anti–Anti–Idiotype Antibodies to *Neisseria gonorrhoeae* Lipooligosaccharides with Bactericidal Activity but No Cross–Reactivity with Red Blood Cell Antigens", *J. Immunol.*, 151(1): 234–243 (1993).

Beucher, et al., "Cloning, Sequencing, and Characterization of the Gene Encoding FrpB, a Major Iron–Regulated, Outer Membrane Protein of *Neisseria gonorrhoeae*", *J. Bacteriol.*, 177(8): 2041–2049 (1995).

Tramont, et al., "Gonococcal Pilus Vaccine. Studies of Antigenicity and Inhibition of Attachment", *J. Clin. Invest.*, 68(4): 881–888 (1981).

Blanco, et al., "Surface Antigens of the Syphilis Spirochete and Their Potential as Virulence Determinants", *Emerg. Infect. Dis.*, 3(1): 11–20 (1997).

Peterson, et al, "Isolation of a *Treponema Pallidum* Gene Encoding Immunodominant Outer Envelope Protein P6, Which Reacts With Sera From Patients at Different Stages of Syphilis", *J. Exp. Med.*, 164(4): 1160–1170 (1986).

Norris, et al., "Polypeptides of *Treponema pallidum*: Progress Toward Understanding Their Structural, Functional, and Immunologic Roles", *Microbiol. Rev.*, 57(3): 750–779 (1993).

Spinola, et al., "The Conserved 18,000–Molecular–Weight Outer Membrane Protein of *Haemophilus ducreyi* Has Homology to PAL", *Infect. Immun.*, 64(6): 1950–1955 (1996).

Hiltke, et al., "Characterization of a Novel Lipoprotein Expressed by *Haemophilus ducreyi*", *Infect. Immun.*, 64(12): 5047–5052 (1996).

Stevens, et al., "A Hemoglobin–Binding Outer Membrane Protein is Involved in Virulence Expression by *Haemophilus ducreyi* in an Animal Model", *Infect. Immun.*, 64(5): 1724–1735 (1996).

Elkins, et al., "Characterization of the hgbA Locus Encoding a Hemoglobin Receptor from *Haemophilus ducreyi*", *Infect. Immun.*, 63(6): 2194–2200 (1995).

Alfa, et al., "Identification of Highly Conserved and Species–Specific Polypeptides of *Haemophilus ducreyi*", *J. Med. Microbiol.*, 37(6): 413–419 (1992).

*New Trends and Developments in Vaccines,* edited by Voller et al., University Park Press, Baltimore, Maryland (1978). Table of Contents only.

* cited by examiner

METHODS OF TREATING HUMAN FEMALES SUSCEPTIBLE TO HSV INFECTION

CROSS-REFERENCES TO RELATED APPLICATIONS

This is a continuation-in-part of PCT/EP99/06623 filed Sep. 8, 1999 and of its U.S. National Phase application filed simultaneously with this application.

STATEMENT REGARDING FEDERALLY SPONSORED RESEARCH OR DEVELOPMENT

Not Applicable

MICROFICHE APPENDIX

Not applicable

BACKGROUND OF THE INVENTION

Pathogens which cause sexually transmitted diseases (STDs) are known and there is an urgent need for effective vaccines to treat or prevent such conditions.

Sometimes sexually transmitted diseases are caused by one or more pathogens. Combination vaccines, able to prevent and/or treat, one or more STDs are therefore also required.

It has been found that certain vaccine formulations are surprisingly efficacious in preventing or treating STDs in female human subjects who are susceptible to or suffering from such STDs.

BRIEF SUMMARY OF THE INVENTION

The present invention relates to one or more antigens for the prevention or treatment of sexually transmitted diseases and the use thereof in the formulation of a vaccine, for administration to female human subjects, for the prevention or treatment of infections associated with pathogens which cause sexually transmitted diseases. The invention also relates to a method of administering the vaccine to females to prevent or treat infections associated with pathogens which cause sexually transmitted diseases.

BRIEF DESCRIPTION OF THE SEVERAL VIEWS OF THE DRAWING(S)

Not Applicable

DETAILED DESCRIPTION OF THE INVENTION

The present invention provides a method of treating a female human subject suffering from or susceptible to one or more sexually transmitted diseases (STDs), which method comprises administering to a female subject in need thereof an effective amount of a vaccine formulation comprising one or more antigens derived from or associated with a STD-causing pathogen and an adjuvant.

Preferably the adjuvant is a TH-1 inducing adjuvant.

In a related aspect the invention provides the use of one or more antigens derived from or associated with a std-causing pathogen and an adjuvant, especially a th-1 inducing adjuvant, in the preparation of a vaccine for administration to a human female subject for the prevention and/or treatment of one or more stds.

Examples of antigens derived from or associated with a STD-causing pathogen include those derived from or associated with herpes viruses (HSV-1 and HSV-2), human papillomaviruses (HPV-all types), *Chlamydia trachomatis*, *Neiserria gonorrhea*, *Treponema pallidum* (syphilis) and *Haemophilus ducreyi* (chancroid).

Other sources of antigens including recombinant bacteria, recombinant viruses, fusion proteins, peptides and mimotopes may also be used.

The above list is not exhaustive and other pathogens are well known to medical practitioners and others skilled in the art and are listed in standard textbooks.

Suitable adjuvants for use in the invention include those well known in the art of vaccine formulation. By 'TH-1 inducing adjuvant' is meant an adjuvant which is a preferential stimulator of TH1 cell response.

A recognised signal that a TH1 response has been stimulated is the enhanced production of TH1-type cytokines eg. IFN-γ and IL-2. IFN-γ secretion is associated with protective responses against intracellular pathogens, including parasites, bacteria and viruses. Activation of leucocytes by IFN-γ enhances killing of intracellular pathogens and increases expression of Fc receptors. Direct cytotoxicity may also occur, especially in synergism with lymphotoxin (another product of TH1 cells). IFN-γ is also both an inducer and a product of NK cells, which are major innate effectors of protection. TH1 type responses, either through IFN-γ or other mechanisms, provide preferential help for murine IgG2a immunoglobulin isotypes.

In contrast, TH-2 type responses are associated with humoral mechanisms and the secretion of IL-4, IL-5, IL-6, IL-10 and tumour necrosis factor-beta.

Adjuvants which are capable of preferential stimulation of the TH1 cell response are described in International Patent Application Nos. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem Montana. A preferred 'small particle' form of 3 De-O-acylated monophosphoryl lipid A is disclosed in EP 0 689 454B1 (SmithKline Beecham Biologicals SA).

In such 'small particle' 3D-MPL the particles of 3D-MPL are small enough to be sterile filtered through a 0.22 micron membrane (as described in European Patent number 0 689 454).

Another preferred adjuvant which may be used in the present invention comprises QS21, an Hplc purified non-toxic fraction derived from the bark of *Quillaja Saponaria Molina*. Optionally this may be admixed with 3D-MPL, optionally together with an carrier.

The method of production of QS21 is disclosed (as QS21) in U.S. Pat. No. 5,057,540 and is available from Aquilla Pharmaceuticals.

Non-reactogenic adjuvant formulations containing QS21 have been described previously (WO 96/33739). Such formulations comprising QS21 and cholesterol have been shown to be successful TH1 stimulating adjuvants when formulated together with an antigen. Thus vaccine compositions which form part of the present invention may include a combination of QS21 and cholesterol.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL:QS21.

Preferably a carrier is also present in the vaccine composition according to the invention. The carrier may be an oil in water emulsion, or an aluminium salt. Other mineral salts may also be used as a carrier such as salts of calcium, iron or zinc. Other carriers include polyphosphazene, liposomes and ISCOMS.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline. A preferred oil-in-water emulsion comprises a metabolisible oil, such as squalene, alpha tocopherol and Tween 80. Additionally the oil in water emulsion may contain span 85 and/or lecithin.

Typically for human administration QS21 and 3D-MPL will be present in a vaccine in the range of 1 µg–500 µg, such as 10–100 µg, preferably 10 µg–50 µg per dose. Typically the oil in water will comprise from 2 to 10% squalene, from 2 to 10% alpha tocopherol and from 0.3 to 3% tween 80. Preferably the ratio of squalene: alpha tocopherol is equal or less than 1 as this provides amore stable emulsion. Span 85 may also be present at a level of 1%. In some cases it may be advantageous that the vaccines of the present invention will further contain a stabiliser.

A particularly potent adjuvant formulation involving QS21, 3D-MPL and tocopherol in an oil in water emulsion is described in WO 95/17210.

In a preferred aspect aluminium hydroxide (alum) or aluminium phosphate will be included in the vaccine composition which is used or manufactured according to the invention.

In a particularly preferred aspect the antigens in the vaccine composition used or manufactured according to the invention are combined with 3D-MPL and alum.

Vaccines employed in the present invention may, if desired, comprise adjuvant molecules of general formula (I):

$$HO(CH_2CH_2O)_n\text{—}A\text{—}R$$

wherein, n is 1–50, A is a bond or —C(O)—, R is $C_{1-50}$alkyl or Phenyl $C_{1-50}$alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck Index ($12^{th}$ ed: entry 7717).

HSV-2 is the primary etiological agent of herpes genitalis. HSV-1 is the causative agent of herpes labialis. Together, these viruses are characterised by their ability to induce both acute diseases and to establish a latent infection, primarily in neuronal ganglia cells.

WO 92/16231 provides further background information about genital herpes and describes a vaccine which can be used to treat people susceptible to HSV infections comprising HSV glycoprotein D or an immunological fragment thereof in conjunction with 3-O-deacylated monophosphoryl lipid A and a suitable carrier.

The specification of WO 92/16231 provides details of glycoprotein D, immunological fragments thereof, and 3D-MPL and methods for obtaining it. The specification describes some promising tests of a candidate vaccine in animal models but no data in humans are given.

In a preferred aspect the method or use according to the invention relates to the prevention or treatment of infections associated with genital herpes, in particular HSV-2 infections.

The vaccine which may be used in the present invention comprises glycoprotein D or an immunological fragment thereof which is typically from HSV-2.

Glycoprotein D is located on the viral membrane, and is also found in the cytoplasm of infected cells (Eisenberg R. J. et al; J of Virol 1980 35 428–435). It comprises 393 amino acids including a signal peptide and has a molecular weight of approximately 60 kD. Of all the HSV envelope glycoproteins this is probably the best characterised (Cohen et al J. Virology 60 157–166). In vivo it is known to play a central role in viral attachment to cell membranes. Moreover, glycoprotein D has been shown to be able to elicit neutralising antibodies in vivo (Eing et al J. Med. Virology 127: 59–65). However, latent HSV-2 virus can still be reactivated and induce recurrence of the disease despite the presence of high neutralising antibodies titre in the patients sera.

As described in WO 92/16231, a preferred embodiment thereof is a truncated HSV-2 glycoprotein D of 308 amino acids which comprises amino acids 1 through 306 of the naturally occurring glycoprotein with the addition of aparagine and glutamine at the C-terminal end of the truncated protein devoid of its membrane anchor region. This form of the protein includes the signal peptide which is cleaved to yield a mature 283 amino acid protein. The production of such a protein in Chinese Hamster Ovary cells has been described in EP-B-139 417.

The mature truncate preferably used in the vaccine formulation within the scope of the invention may be designated recombinant gD2t (rgD2t) or simply (as hereinbelow) gD2t.

The HSV antigen may be chemically or otherwise conjugated to a particulate carrier as described in WO 92/16231.

In one preferred aspect the vaccine for use in the invention comprises gD2t, 3D-MPL (especially small particle 3D-MPL) and aluminium hydroxide (alum).

Papillomaviruses are small DNA tumour viruses, which are highly species specific. As yet, over 70 individual human papillomavirus (HPV) genotypes have been described. HPVs are generally specific either for the skin (eg HPV-1 and -2) or mucosal surfaces (eg HPV-6 and -11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma. Cervical cancer is the most common malignancy in developing countries, with about 500,000 new cases occuring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293–306 and Hagenesee M. E., Infections in Medicine 1997 14(7) 555–556, 559–564. Preferably a vaccine composition according to the invention comprises the major capsid protein, the L1 protein.

Today, the different types of HPVs have been isolated and characterised with the help of cloning systems in bacteria and more recently by PCR amplification. The molecular organisation of the HPV genomes has been defined on a comparative basis with that of the well characterised bovine papillomavirus type 1 (BPV1).

Although minor variations do occur, all HPVs genomes described have at least seven early genes, E1 to E7 and two late genes L1 and L2. In addition, an upstream regulatory region harbors the regulatory sequences which appears to control most transcriptional events of the HPV genome.

E1 and E2 genes are involved in viral replication and transcriptional control, respectively and tend to be disrupted by viral integration. E6 and E7, and recent evidence implicate also E5 are involved in viral transformation.

In the HPVs involved in cervical carcinoma such as HPV 16 and 18, the oncogenic process starts after integration of viral DNA. The integration results in the inactivation of genes coding for the capsid proteins L1 and L2 and in installing continuously over expression of the two early proteins E6 and E7 that will lead to gradually loss of the normal cellular differentiation and the development of the carcinoma.

Carcinoma of the cervix is common in women and develops through a pre-cancerous intermediate stage to the invasive carcinoma which frequently leads to death. The intermediate stages of the disease is known as cervical intraepithelial neoplasia and is graded I to III in terms of increasing severity.

Clinically, HPV infection of the female anogenital tract manifests as cervical flat condylomas, the hallmark of which is the koilocytosis affecting predominantly the superficial and intermediate cells of the cervical squamous epithelium.

Koilocytes which are the consequence of a cytopathic effect of the virus, appear as multinucleated cells with a perinuclear clear haloe. The epithelium is thickened with abnormal keratinisation responsible for the warty appearance of the lesion.

Such flat condylomas when positive for the HPV 16 or 18 serotypes, are high-risk factors for the evolution toward cervical intraepithelial neoplasia (CIN) and carcinoma in situ (CIS) which are themselves regarded as precursor lesions of invasive cervix carcinoma.

International Patent Application No. WO 96/19496 discloses variants of human papilloma virus E6 and E7 proteins, particularly fusion proteins of E6/E7 with a deletion in both the E6 and E7 proteins. These deletion fusion proteins are said to be immunogenic.

HPV L1 based vaccines are disclosed in WO94/00152, WO94/20137, WO93/02184 and WO94/05792. Such a vaccine can comprise the L1 antigen as a monomer, a capsomer or a virus like particle. Such particles may additionally comprise L2 proteins. Other HPV vaccines are based on the Early proteins, such as E7 or fusion proteins such as L2-E7.

In the vaccine of the invention it is preferred to utilise compositions comprising either an E6 or E7 protein linked to an immunological fusion partner having T cell epitopes.

In a preferred form of the invention, the immunological fusion partner is derived from protein D of *Heamophilus influenza* B. Preferably the protein D derivative comprises approximately the first ⅓ of the protein, in particular approximately the first N-terminal 100–110 amino acids.

Accordingly, the present invention may employ fusion proteins comprising Protein D-E6 from HPV 16, Protein D-E7 from HPV 16 Protein D-E7 from HPV 18 and Protein D-E6 from HPV 18. The protein D part preferably comprises the first ⅓ of protein D.

The obligate intracellular bacteria *Chlamydia trachomatis* infects mucosal epithelial cells of the conjunctiva and of the urogenital tract, causing a wide spectrum of human diseases such as trachoma and genital infections which can result in long term sequelae. Trachoma, which is endemic in several developing countries, is the world's leading cause of preventable blindness; genital infections, which represent around 3 million cases per year in the US, rend annually 200,000 women infertile following *Chlamydia salpingitis* (Washington, et al., JAMA, 257:2070–2072, 1987). Therefore, this pathogen is a significant public health problem and efforts are made to set up a vaccine against human Chlamydia infections.

Vaccine trials performed in man and non-human primates using the whole organism as immunogen gave serovar-specific protection but some of the vaccinees developed more severe reactions upon reinfection (Grayston, et al., The Journal of Infectious Diseases, 132:87–105, 1975). Several studies have demonstrated that the pathology associated with Chlamydia infection is immunologically mediated (Grayston, et al., Reviews of Infectious Diseases, 7:717–725, 1985); moreover, a purified Chlamydia 57 kDa (Hsp60) was shown to elicit a pathology similar to reinfection in animals previously infected (Morrison, et al., J. Exp. Med., 170:1271–1283, 1989; Blander, et al., Infec. Immun., 62:3617–3624, 1994). This observation led to the conclusion that protection against *Chlamydia trachomatis* could only be achieved using a subunit vaccine.

The *Chlamydia trachomatis* species is stereotyped into 15 serovars which are placed into 3 serogroups: the B complex (serovars B, Ba, D, E, L1 and L2), the intermediate complex (serovars F, G, K, L3) and the C complex (serovars A, C, H, I and J) (Wang, et al., The Journal of Infectious Diseases, 152:791–800, 1985). Sexually transmitted diseases (STD) are caused by serovars D to K which cover the 3 serogroups. Thus a subunit vaccine against Chiamydia STD should protect against multiple serovars that are more or less antigenically related.

For the design of a subunit vaccine, much interest has been focused on the serotyping antigen which consist in the 40 kDa major outer membrane protein (MOMP). This protein which was shown to function in vitro as a porin (Bavoil, et al., Infect. Immun., 44:479–485, 1984), is present during the whole life cycle of the bacteria (Hatch, et al., J. Bacteriol., 165:379–385, 1986); this principal surface protein is highly immunogenic in humans and animals. The MOMP display 4 variable domains (VD) surrounded by five constant regions that are highly conserved among serovars (Stephens, et al., J. Bacteriol., 169:3879–3885, 1987; Yuan, et a., Infect. Immun., 57:1040–1049, 1989). In vitro and in vivo neutralizing B-cell epitopes have been mapped on VDs (Baehr, et al., Proc. Natl. Acad. Sci., USA, 85:4000–4004, 1988; Lucero, et al., Infect. Immun., 50:595–597, 1985; Zhang, et al., J. Immunol., 138:575–581, 1987; Peterson, et al., Infect. Immun., 56:885–891, 1988; Zhang, et al., Infect. inmun., 57:636–638, 1989) whereas T-cell epitopes have been identified in both variable and constant domains (Allen, et al., J. Immunol., 147:674–679, 1991; Su, et al., J. Exp. Med., 172:203–212, 1990). Recombinant MOMP has been expressed in *E. coli* by, different authors (Manning, et al., 61:4093–4098, 1993; Koehler, et al., Molecular Microbiology, 6:1087–1094, 1992; Pickett, et al., Molecular Microbiology, 2:681–685, 1988); however, Manning et al. shown that their recombinant protein failed to react with a monoclonal antibody that recognize a conformational MOMP epitope (Manning, et al., Infect. Immun., 61:4093–4098, 1993).

Immunizations with recombinant or purified MOMP followed by homotypic or heterotypic Chlamydia challenge have been performed in different animal models with variable effects on the parameters of the infection (Taylor, et al., Investigative Ophthalmology and Visual Science, 29:1847–1853, 1988; Batteiger, et al., Journal of General Microbiology, 139:2965–2972, 1993; Tuffrey, et al., Journal of General Microbiology, 138:1707–1715, 1992). An elegant experimental model of *salpingitis* has been developed in mice in which intrauterine inoculation of a human strain of *Chlamydia trachomatis* leads to long term infertility (Tuffrey, et al., Br. J. Exp. Path., 67:605–616, 1986; Tuffrey, et al., Br. J. Exp. Path., 78:251–260, 1986). In a heterotypic challenge experiment, Tuffrey et aL have shown that parenteral and mucosal immunization with rMOMP absorbed on alhydrogel reduced the severity of the *salpingitis* and the duration of the lower genital tract colonization, respectively. However, the preparation conferred no protection against infertility resulting from infection (Tuffrey, et al., Journal of General Microbiology, 138:1707–1715, 1992).

Both cell mediated and humoral immunity seem to play a protective role in the genital pathologies caused by *Chlamydia trachomatis*. However, Rank's group suggests that in mice T-cell mediated immunity is the principal immune mechanism for controlling chlamydial genital disease (Ramsey, et al., Infect. Immun., 56:1320–1325, 1988; Rank, et al., Infect. Immun., 48:847–849, 1985; Igietseme, et al., Infect. immun., 59:1346–1351, 1991) and CD4 and CD8 positive T-cells have been shown to contribute to antichlamydial immunity in vivo (Igietseme, et al., Regional Immunology, 5:317–324, 1993; Igietseme, et al., Infect. Immun., 62:5195–5197, 1994).

In an embodiment of the invention the MOMP antigen is from Serovar 2 and is produced in *E.coli* by means of recombinant DNA techniques. In such circumstances the protein is produced without its signal sequence.

Antigens derived from or associated with *N. gonorrhoea* include transferrin binding protein (Thp). Two proteins are involved in making the Thp complex—ThpA and TbpB. The gonococcal ThpA DNA/protein sequence is disclosed in WO 92/03467 (University of North Carolina). A recent paper that refers specifically to ThpA and TbpB of gonococcus and how they are required for infection is Mol. Microbiol., February 1998; 27 (3): 611–616. Other antigens include the Por B protein, see Proc Natl Acad Sci USA November 1987; 84 (22):8135–8139 and Mol Biol Evol May 1995; 12 (3):363–370. Yet a further antigen is a lipopolysaccharide (R type) described in Can J Microbiol February 1978; 24 (2):117–123. See also J Immunol July 1993 1;151 (1):234–243. The FrpB protein is also a candidate antigen; see J Bacteriol April 1995; 177 (8):2041–2049 and WO 96/31618. A Pilus vaccine is described in J Clin Invest October 1981; 68 (4):881–888.

Antigens derived from or associated with the pathogen for syphilis include outer membrane proteins of Treponema; see Emerg Infect Dis January 1997; 3 (1): 11–20. A unique physical feature of *Treponema pallidum*, the venereally transmitted agent of human syphilis, is that its outer membrane contains 100-fold less membrane-spanning protein than the outer membranes of typical gram-negative bacteria, a property that has been related to the chronicity of syphilitic infection. These membrane-spanning *T. pallidum* rare outer membrane proteins, termed TROMPs, represent potential surface-exposed virulence determinants and targets of host immunity. The outer membrane of *T. pallidum* been isolated and its constituent proteins identified. Five proteins of molecular mass 17-, 28-, 31-, 45-, and 65-kDa were outer membrane associated. Tromps 1, 2, and 3 were antigenic when tested with serum from infection and immune syphilitic rabbits and humans. A further candidate is outer envelope protein P6; see J Exp Med October 1986 1;164 (4):1160–1170. See also Microbiol Rev September 1993; 57 (3):750–779.

Chancroid is a sexually transmitted diseased caused by *Haemophilus ducreyi*. Antigens derived from or associated with *Haemophilus ducreyi* include a 18,000 MW outer membrane protein described in Infect Immun June 1996; 64 (6): 1950–1955. A novel lipoprotein expressed by *Haemophilus ducreyi* is described in Infect Immun December 1996; 64 (12):5047–5052 A hemoglobin-binding outer membrane protein is involved in virulence expression by *Haemophilus ducreyi* in an animal model. See Infect Immun May 1996; 64(5):1724–1735. Characterization of the hgbA locus encoding a hemoglobin receptor from *Haemophilus ducreyi* is described in Infect Immun June 1995; 63 (6):2194–2200. See also J Med Microbiol December 1992; 37 (6):413–419 for identification of highly conserved and species-specific polypeptides of *Haemophilus ducreyi*.

Combination vaccines adminstered or prepared according to the present invention will contain an immunoprotective quantity of the antigens and may be prepared and administered by conventional techniques.

Vaccine preparation is generally described in New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of antigen in each vaccine dose is selected as an amount which induces an immunoprotective or therapeutic response without significant, adverse side effects in typical vaccinees. Such amount will vary depending upon which specific immunogen is employed. Generally, it is expected that each dose will comprise 1–1000 µg of protein, preferably 2–100 µg, most preferably 4–40 µg. An optimal amount for a particular vaccine can be ascertained by standard studies involving observation of antibody titres and other responses in subjects. Following an initial vaccination, subjects may receive a boost in about 4 weeks.

The amount of antigen in each vaccine dose is an amount which induces an immunoprotective or therapeutically effective response without significant adverse side effects in typical female vaccinees.

Generally it is expected that each dose will comprise 1–1000 µg of antigen, preferably 2–100 µg, most preferably 4–40 µg. The TH-1 inducing adjuvant, for example 3D-MPL, will normally be present in a range of 10–200 µg, preferably 25–75 µg, especially about 50 µg per dose.

The amount of carrier may vary and may be selected according to the knowledge of one skilled in the art. If aluminium hydroxide (alum) or aluminium phosphate is used the amount employed will generally be in the range 100–1000 µg, for example 250–750 µg, preferably about 500 µg per vaccine dose.

Typical amounts of each component in the vaccine are antigen (20 µg), alum (500 µg) and an adjuvant, especially a TH-1 inducing adjuvant such as 3D-MPL (50 µg).

In one preferred aspect the vaccine for use in the invention comprises gD2t, 3D-MPL (especially small particle 3D-MPL) and aluminium hydroxide (alum).

In one preferred regimen the vaccine may be given at intervals of 0, 1 and 6 months. Other dosing regimens, including booster doses, may also be used. The vaccine may be administered intramuscularly.

The manufacture of a vaccine according to the invention may be accomplished by conventional techniques, such as described in WO 92/16231. The method typically involves mixing one or more antigens derived from or associated with an STD with an adjuvant, especially a TH-1 inducing adjuvant, and optionally a carrier as hereinabove described. The resulting vaccine composition may be used for administration to female subjects according to the method of the invention, especially sexually active women suffering from or at risk of contracting an STD.

Generally the women will be in an age range of 12–70 years, more usually adolescents and women of 60 or less, for example 14–60, typically 18–45 as in the study described below. In one aspect a suitable group of women includes those suffering from or at risk of contracting genital herpes infection. The method or use of the invention may, for example, be applied in seronegative healthy consorts of subjects with genital herpes disease.

The invention is illustrated, without limitation, by the following examples, showing results when a herpes vaccine was administered to female subjects. Similar results may be obtained with vaccines against other STDs such as HPV and chlamydia antigens and with combination or polyvalent vaccines against more than one STD, especially combination vaccines comprising an antigen associated with Herpes Simplex, more especially HSV-2 gD or immunological fragments thereof such as gD2t as hereinabove described.

EXAMPLE 1

Design of study

Vaccine Under Study

SmithKline Beecham Biologicals Herpes simplex candidate vaccine (gD2t—20 µg) with Alum (500 µg) and 3D-MPL (50 µg).

Title

A double-blind, randomized, placebo-controlled study to evaluate the efficacy of SmithKline Beecham Biologicals' Herpes Simplex candidate vaccine (gD2t) with 3D-MPL to prevent genital herpes disease in healthy consorts of subjects with genital herpes disease.

Indication/study Population

Healthy adult volunteers, male and female, aged 18 to 45 years with negative serological markers of Herpes Simplex infection (HSV-1 and -2) and whose consort has clinical genital herpes disease.

Objectives of the Study

Primary

To compare with placebo, during the 17 month period starting one month after the second vaccination, the protective efficacy of gD-Alum-3D-MPL vaccine to prevent genital herpes clinical disease.

Secondary

To compare with placebo, starting one month after the second vaccination, the protective efficacy of gD-Alum-3D-MPL vaccine to prevent genital herpes infection.

To compare with placebo after the full vaccination course, the protective efficacy of gD-Alum-3D-MPL vaccine to prevent genital herpes infection.

To compare with placebo, after the full vaccination course, the protective efficacy of gD-Alum-3D-MPL vaccine to prevent genital herpes infection during a period of extended clinical follow-up.

To compare with placebo, after the full vaccination course, the protective efficacy of gD-Alum-3D-MPL vaccine to prevent genital herpes disease.

To compare with placebo, after the full vaccination course, the protective efficacy of gD-Alum-3D-MPL vaccine to prevent genital herpes clinical disease during a period of extended clinical follow-up.

To evaluate, starting one month after the second vaccination, the time to occurrence of disease in each group.

To evaluate, starting one month after the second vaccination, the time to occurrence of infection in each group.

To evaluate, in each group, the number of typical and atypical cases of genital herpes disease.

To evaluate the severity of primary disease in both groups.

To evaluate the humoral and cellular immune response (excluding subjects from study centers initiated after Jul. 1, 1995) of the vaccine.

To determine serological or immunological correlates for protective efficacy (excluding subjects from study centers initiated after Jul. 1, 1995). In case of primary disease or infection, to evaluate the number of subsequent recurrences in the two groups.

To evaluate the safety and reactogenicity of SmithKline Beecham Biologicals' herpes simplex candidate vaccine (with 3D-MPL) in healthy HSV seronegative subjects.

To evaluate the number of cases of oro-labial (or non-genital) herpes disease.

To compare with placebo, starting one month after the second vaccination, the protective efficacy of gD-Alum-3D-MPL to prevent suspected genital herpes signs and symptoms associated with either Western Blot seroconversion to non-vaccinal antigens or with the detection of HSV DNA in a genital swab by PCR.

To evaluate the incidence of genital herpes disease and HSV infection in vaccine recipients during the period of extended clinical follow-up.

Study Design

Double-blind, Randomized, Placebo-controlled Study

Vaccination schedule: 0-1-6 months.

Initial follow-up period-17 months for each subject starting 1 month after the second vaccination.

Extended follow-up period- 24 months for each subject (from the month 19 visit to the month 43 visit)

Phase A (double blind, vaccine and placebo recipients)- ends when the last subject enrolled completes the initial follow-up period (around the time that the study is unblinded for analysis).

Phase B (open, vaccine recipients only)- begins when the last subject enrolled completes the initial follow-up period (month 19 visit) and ends when the last subject enrolled completes the month 43 visit.

Because there may be a period of several months between the date that the last subject enrolled completes the initial follow-up period and the date that the study is fully unblinded for analysis, (due to the time required for encoding and cleaning of all of the study data collated during the initial follow-up period and phase A of the extended follow-up period), the initial part of phase B of the extended follow-up period may include both vaccine and placebo recipients.

2 groups:

I. gD2t-Alum-3D-MPL

Alum-3D-MPL as placebo

Schematic of HSV-007 Study Design-Study Periods

Vaccination (V) phase;

Initial follow-up* (initial f/u*);

Extended follow-up phase A; Extended follow-Up phase B.

*Note: The modified "initial follow-up period" now includes months 2–19

Number of Subjects 800 couples will be enrolled into the study to allow for at least 640 evaluable subjects.

Primar Efficacy Endpoint

During the 17-month period, starting one month after the second vaccination (months 2–19), the primary efficacy end-point will be as follows:

Prevention of Disease

A comparison between the two groups of the number of subjects with at least one compatible symptom of genital herpes disease AND either a concurrent positive culture OR appearance of antibodies to non-vaccinal antigens by Western Blot within six months and positive local detection of herpes simplex DNA by Polymerase Chain Reaction (PCR).

|  | Clinical Symptom | Culture | Antibodies to non-vaccinal antigens | PCR |
|---|---|---|---|---|
| Disease | + | + | +/– | NA |
|  | + | – | + | + |

NA: Not Applicable

Secondary Efficacy Endpoints

1) Prevention of infection:

A comparison will be made (between vaccine and placebo groups), of the number of subjects who develop antibodies to non-vaccinal antigens (seroconversion) and of subjects who develop disease (culture proven).

This endpoint will be evaluated for the following periods:

Initial period of follow-up (months 2–19)

Months 7–19

Phase A of the extended follow-up

Initial period of follow-up (months 2–19) and phase A of the extended follow-up combined.

Months 7–19 and phase A of the extended follow-up combined.

The analysis of data from phase A of the extended follow-up period will include all events occurring after each subject's month 19 visit and the end of phase A (when the last subject enrolled completes the month 19 visit).

| Case definition | | | | |
|---|---|---|---|---|
|  | Clinical Symptom | Culture | Antibodies to non-vaccinal antigens | PCR |
| Infection Disease | + | + | +/– | NA |
| Infection Disease | + | – | + | + |
| Infection | +/– | NA | + | NA |

NA: Not Applicable

2) Prevention of disease between months 7–19

A comparison with placebo after the full vaccination course (months 7–19) of the number of subjects with at least one compatible symptom of genital herpes disease AND either a concurrent positive culture OR appearance of antibodies to non-vaccinal antigens by Western Blot and positive local detection of herpes simplex DNA by Polymerase Chain Reaction (PCR).

3) Prevention of disease during phase A of the extended follow-up period

During phase A of the extended follow-up period, a comparison will be performed between the two groups of the number of subjects with at least one compatible symptom of genital herpes disease AND either a concurrent positive culture OR appearance of antibodies to non-vaccinal antigens by Western Blot and positive local detection of herpes simplex DNA by Polymerase Chain Reaction (PCR).

In addition, this endpoint will also be evaluated for the new initial follow-up period (months 2–19) and phase A of the extended follow-up period combined and also for months 7–19 and phase A of the extended follow-up combined.

4) To evaluate during the 17 month period starting one month after the second vaccination, in each group, the time to occurrence of genital herpes disease.

5) To evaluate during the 17 month period starting one month after the second vaccination, in each group, the time to occurrence of genital herpes infection.

6) To evaluate in each group the number of cases of typical genital herpes clinical disease and of atypical genital herpes disease.

The case definitions are described in the primary endpoint.

7) To evaluate in each group the patient's subjective local and general signs and symptoms of genital HSV disease and their duration.

8) To evaluate the humoral (anti-gD2 antibodies by ELISA and anti-HSV neutralizing antibodies) and cellular (lymphoproliferation, secretion of gamma interferon) response to the vaccine (excluding subjects from study centers initiated after Jul. 1, 1995).

9) If clinical efficacy is demonstrated, serological and immunological markers will be extensively evaluated using the sera and Peripheral Blood Lymphocytes stored when scheduled, in an attempt to determine correlates between protective efficacy and laboratory parameters (excluding subjects from study centers initiated after Jul. 1, 1995).

10) In case of primary disease or infection, to evaluate the number of subsequent recurrences of genital herpes in each group.

11) The local and general reactogenicity and the safety will be evaluated after each vaccination by recording the local and general signs and symptoms after each dose and the adverse experiences during the study course. The haematological and biochemical parameters will be checked at baseline and after the last vaccination.

During the extended follow-up period, all serious adverse experiences reported by vaccine recipients will be recorded.
12) To evaluate the number of clinical cases of non-genital herpes disease, including oro-labial herpes disease, in each group.
13) To compare with placebo, during the 17 month follow-up period, starting one month after the second vaccination, the number of vaccine recipients who develop genital herpes signs and symptoms associated with either seroconversion to non-vaccinal antigens by Western Blot (within a six month period from the onset of genital herpes signs or symptoms) or with the detection of HSV DNA in a genital swab by PCR.
14) During phase B of the extended follow-up period, the number of vaccine recipients who develop antibodies to non-vaccinal antigens (seroconversion) and of subjects who develop disease (culture proven) will be analyzed in relationship to the interval since administration of last vaccination. These data will be used to calculate the attack rate of genital herpes disease and infection.

EXAMPLE 2

The analysis of the primary endpoint is based on comparison of attack rates between the vaccine and placebo groups as described in the RAP. The analysis of the secondary endpoints is based on either comparison of attack rates or comparison of time to occurrence of disease or infection endpoints as described below.

Statistical tests are two-sided and performed using SAS software and an $\alpha$-level of 0.05. It should be noted that many statistical analyses are reported, but for the secondary endpoints the error rate ($\alpha$) is not under control. Since no adjustments of the $\alpha$ were performed for the secondary endpoints, the p-values must be interpreted cautiously and as descriptive only.

Populations Analysed for Vaccine Efficacy

Efficacy analyses are performed on two subject populations: the intention-to-treat population (ITT) and the according-to-protocol population (ATP). The ATP group is also referred to hereinbelow as the per-protocol (PP) group.

The analysis of the according-to-protocol population is the primary analysis. The definition of the ATP (or PP) population is defined by the study period under consideration:

1) For the period between months 2–19, the ATP population consists of subjects:
   who meet all protocol eligibility criteria
   who have received three doses of vaccine/placebo
   or who have received two doses of vaccine/placebo and for whom the considered event (disease or infection) has occurred prior to the month 6 visit
   for whom the considered event (disease or infection) has not occurred before the start of the month 2–19 period.
2) For the period between months 7–19, the ATP population consists of subjects:
   who meet all protocol eligibility criteria
   who have received three doses of vaccine/placebo
   for whom the considered event (disease or infection) has not occurred before the start of the month 7–19 period.

The analysis of the ITT population is considered as the secondary analysis. This analysis includes all subjects who received at least one dose of study vaccine and have at least one on-vaccine assessment.

The purpose of the two analyses is to ensure that protocol violations, subject dropouts and withdrawals are not treatment related and do not lead to any selection bias in the efficacy results.

The populations to be included in the immunogenicity and safety analyses will be fully described in the final study report.

Evaluation Periods

The evaluation periods during which analyses are performed include:

months 2–19 (ATP population)

months 7–19 (ATP population)

months 0–19 (IT population)

Selected results are shown below, together with a summary of the overall conclusions of the study.

TABLE 1a

Adjustment of vaccine effect on the occurrence of genital herpes disease by gender-ITT population

| Terms fitted in the model | Deviance | Degrees of freedom | p-value |
|---|---|---|---|
| treatment group | 320.5561 | 845 | |
| treatment group, gender | 317.2083 | 844 | 0.067 |
| treatment group, gender, and the interaction | 312.0443 | 843 | 0.023 |

TABLE 1b

Adjustment of vaccine effect on the occurrence of genital herpes infection by gender-ITT population

| Terms fitted in the model | Deviance | Degrees of freedom | p-value |
|---|---|---|---|
| treatment group | 510.8654 | 845 | |
| treatment group, gender | 494.9266 | 844 | <0.001 |
| treatment group, gender, and the interaction | 491.5551 | 843 | 0.066 |

Distribution of Genital Herpes Disease and HSV Infection Cases by Treatment Group TABLE 2a Genital Herpes Disease Cases by Treatment Group-Males and Females

| | Intention-To-Treat (N = 847) | | Per-Protocol* | |
|---|---|---|---|---|
| Interval | Vaccine (425) | Placebo (422) | Vaccine | Placebo |
| M 0–2 | 2 | 7 | | |
| M 2–7 | 9 | 8 | | |
| M 7–19 | 4 | 9 | 3 (349) | 7 (349) |
| M 2–19 | 13 | 17 | 12 (371) | 16 (369) |
| >M19 | 1 | 0 | | |
| Total | 16 | 24 | | |

*For each interval, the number of per-protocol evaluable subjects is shown in the ()

TABLE 2b

Genital Herpes Disease Cases by Treatment Group-Males only

| | Intention-To-Treat (N = 579) | | Per-Protocol* | |
|---|---|---|---|---|
| Interval | Vaccine (288) | Placebo (291) | Vaccine | Placebo |
| M 0–2 | 2 | 2 | | |
| M 2–7 | 6 | 5 | | |
| M 7–19 | 3 | 3 | 2 (240) | 2 (247) |
| M 2–19 | 9 | 8 | 8 (252) | 8 (261) |
| >M19 | 1 | 0 | | |
| Total | 12 | 10 | | |

*For each interval, the number of per-protocol evaluable subjects is shown in the ()

TABLE 2c

Genital Herpes Disease Cases by Treatment Group-Females only

| | Intention-To-Treat (N = 268) | | Per-Protocol* | |
|---|---|---|---|---|
| Interval | Vaccine (137) | Placebo (131) | Vaccine | Placebo |
| M 0–2 | 0 | 5 | | |
| M 2–7 | 3 | 3 | | |
| M 7–19 | 1 | 6 | 1 (109) | 5 (102) |
| M 2–19 | 4 | 9 | 4 (119) | 8 (108) |
| >M19 | 0 | 0 | | |
| Total | 4 | 14 | | |

*For each interval, the number of per-protocol evaluable subjects is shown in the ()

TABLE 3a

Genital Herpes Infection Cases by Treatment Group-Males and Females

| | Intention-To-Treat (N = 847) | | Per-Protocol* | |
|---|---|---|---|---|
| Interval | Vaccine (425) | Placebo (422) | Vaccine | Placebo |
| M 0–2 | 2 | 10 | | |
| M 2–7 | 17 | 13 | | |
| M 7–19 | 11 | 16 | 10 (349) | 16 (349) |
| M 2–19 | 28 | 30 | 26 (371) | 29 (369) |
| >M19 | 5 | 2 | | |
| Total | 35 | 41 | | |

*For each interval, the number of per-protocol evaluable subjects is shown in the ()

TABLE 3b

Genital Herpes Infection Cases by Treatment Group-Males only

| | Intention-To-Treat (N = 579) | | Per-Protocol* | |
|---|---|---|---|---|
| Interval | Vaccine (288) | Placebo (291) | Vaccine | Placebo |
| M 0–2 | 2 | 2 | | |
| M 2–7 | 9 | 8 | | |
| M 7–19 | 6 | 6 | 5 (240) | 6 (247) |
| M 2–19 | 15 | 14 | 13 (252) | 14 (261) |
| >M19 | 3 | 0 | | |
| Total | 20 | 16 | | |

*For each interval, the number of per-protocol evaluable subjects is shown in the ()

TABLE 3c

Genital Herpes Infection Cases by Treatment Group-Females only

| | Intention-To-Treat (N = 268) | | Per-Protocol* | |
|---|---|---|---|---|
| Interval | Vaccine (137) | Placebo (131) | Vaccine | Placebo |
| M 0–2 | 0 | 8 | | |
| M 2–7 | 8 | 5 | | |
| M 7–19 | 5 | 10 | 5 (109) | 10 (102) |
| M 2–19 | 13 | 15 | 13 (119) | 15 (108) |
| >M19 | 2 | 2 | | |
| Total | 15 | 25 | | |

*For each interval, the number of per-protocol evaluable subjects is shown in the ()

Preliminary Efficacy Analysis

Primary Efficacy Endpoint

During the 17-month period, starting one month after the second vaccination (months 2–19), the primary efficacy end-point will be as follows:

Prevention of Disease

A comparison between the two groups of the number of subjects with at least one compatible symptom of genital herpes disease AND either a concurrent positive culture OR appearance of antibodies to non-vaccinal antigens by Western Blot within six months and positive local detection of herpes simplex DNA by Polymerase Chain Reaction (PCR).

TABLE 4a

Prevention of Genital Herpes Disease-Males and Females

| Interval | Population | Efficacy (95% CI) |
|---|---|---|
| All | ITT | 33.8 (−22.8, 64.3%) |
| M 2-19 | PP | 25.4% (−55.5, 64.2%) |

TABLE 4b

Prevention of Genital Herpes Disease-Males only

| Interval | Population | Efficacy (95% CI) |
|---|---|---|
| All | ITT | −21.2 (−176.2, 46.8%) |
| M 2-19 | PP | 3.6% (−171.7, 60.5%) |

TABLE 4c

Prevention of Genital Herpes Disease-Females only

| Interval | Population | Efficacy (95% CI) |
|---|---|---|
| All | ITT | 72.7% (19.1, 90.8%) |
| M 2-19 | PP | 54.6% (−46.4, 85.9%) |

Secondary Efficacy Endpoints

1) Prevention of infection:

A comparison will be made (between vaccine and placebo groups), of the number of subjects who develop antibodies to non-vaccinal antigens (seroconversion) and of subjects who develop disease (culture proven) for the initial period of follow-up (months 2–19).

TABLE 5a

Prevention of Genital Herpes Infection-Males and Females

| Interval | Population | Efficacy (95% CI) |
|---|---|---|
| All | ITT | 15.2% (−30.4, 44.0%) |
| M 2-19 | PP | 10.8% (−48.4, 46.4%) |

TABLE 5b

Prevention of Genital Herpes Infection-Males only

| Interval | Population | Efficacy (95% CI) |
|---|---|---|
| All | ITT | −26.3% (−138.8, 33.2%) |
| M 2-19 | PP | 3.8% (−100.5, 53.9%) |

TABLE 5c

Prevention of Genital Herpes Infection-Females only

| Interval | Population | Efficacy (95% CI) |
|---|---|---|
| All | ITT | 42.6% (−3.9, 68.3%) |
| M 2-19 | PP | 21.3% (−57.7, 60.8%) |

2) Prevention of infection:

A comparison will be made (between vaccine and placebo groups), of the number of subjects who develop antibodies to non-vaccinal antigens (seroconversion) and of subjects who develop disease (culture proven) for months 7–19.

TABLE 6a

Prevention of Genital Herpes Infection-Males and Females

| Interval | Population | Efficacy (95% CI) |
|---|---|---|
| M 7-19 | PP | 37.5% (−35.8, 71.2%) |

TABLE 6b

Prevention of Genital Herpes Infection-Males only

| Interval | Population | Efficacy (95% CI) |
|---|---|---|
| M 7-19 | PP | 14.2% (−177.3, 73.5%) |

TABLE 6c

Prevention of Genital Herpes Infection-Females only

| Interval | Population | Efficacy (95% CI) |
|---|---|---|
| M 7-19 | PP | 53.2% (−32.2, 83.4%) |

3) Prevention of disease between months 7–19

A comparison with placebo after the full vaccination course (months 7–19) of the number of subjects with at least one compatible symptom of genital herpes disease AND either a concurrent positive culture OR appearance of antibodies to non-vaccinal antigens by Western Blot and positive local detection of herpes simplex DNA by Polymerase Chain Reaction (PCR).

TABLE 7a

Prevention of Genital Herpes Disease-Males and Females

| Interval | Population | Efficacy (95% CI) |
|---|---|---|
| M 7-19 | PP | 57.1% (−64.4, 88.8%) |

TABLE 7b

Prevention of Genital Herpes Disease- Males only

| Interval | Population | Efficacy (95% CI) |
|---|---|---|
| M 7–19 | PP | −2.9% (−624.7, 85.4%) |

TABLE 7c

Prevention of Genital Herpes Disease- Females only

| Interval | Population | Efficacy (95% CI) |
|---|---|---|
| M 7–19 | PP | 81.3% (−57.5, 97.8%) |

To evaluate during the 17 month period starting one month after the second vaccination, in each group, the time to occurrence of genital herpes disease.

Time to occurrence of genital herpes disease for the ITT population is shown in FIGS. 1a (males and females), 1b (males only), and 1c (females only). The efficacy analyses of time to occurrence of genital herpes disease for the ITT population is shown in tables 8a (males and females), 8b (males only), and 8c (females only). Time to occurrence was not analyzed for the per-protocol populations (months 2–19) since an early difference in survival without disease was observed between vaccine and placebo recipients prior to month 2.

Note: the time to occurrence analysis excludes genital herpes disease cases occurring after month 19.

TABLE 8a

Prevention of Genital Herpes Disease by Time to Occurrence-Males and Females

| Interval | Population | p-value (Log Rank test) | Efficacy (95% CI) |
|---|---|---|---|
| M 0–19 | ITT | 0.1432 | 37.96% (−18.27, 67.45%) |

TABLE 8b

Prevention of Genital Herpes Disease by Time to Occurrence-Males only

| Interval | Population | p-value (Log Rank test) | Efficacy (95% CI) |
|---|---|---|---|
| M 0–19 | ITT | 0.8025 | −11.54% (−162.55, 52.63%) |

TABLE 8c

Prevention of Genital Herpes Disease by Time to Occurrence-Females only

| Interval | Population | p-value (Log Rank test) | Efficacy (95% CI) |
|---|---|---|---|
| M 0–19 | ITT | 0.013 | 73.24% (18.69, 91.19%) |

Summary and Conclusions After Detailed Analysis of the Results of the Trial

Demographic Characteristics and Risk Factors Evaluation

Overall, of the 847 (425 vaccine and 422 placebo) subjects enrolled, 697 (344 vaccine and 353 placebo) subjects completed the study through to month 19. One hundred and fifty (150) subjects dropped out of the study; none of the drop outs resulted from a serious adverse event.

Three hundred and seventy (370) subjects in the vaccine group and 369 in the placebo group were evaluable in the month 2–19 ATP population. Treatment groups were balanced for all demographic characteristics and the selection of protocol compliers for the ATP population analysis did not result in the introduction of bias by treatment groups.

Risk factors that might impact on the rate of acquisition of genital herpes disease or infection were assessed and included duration of relationship prior to study entry, the mean time until separation from the source partner, the frequency of sexual intercourse (at baseline and during the efficacy follow-up period), and the frequency of condom use (at baseline and during the efficacy follow-up period).

These results indicate that the vaccine and placebo groups were balanced at baseline for all risk factors and the balance was maintained during the study. The similarity of the ITT population profile to that of the ATP population in terms of risk factors also confirms that the elimination of the non-compliers to the protocol did not bias the treatment groups.

Sub-analyses by gender indicates that within each gender group, risk factors that might impact on the acquisition of genital herpes disease or infection are balanced by treatment group.

Primary Efficacy Endpoint Analysis

The analysis of the primary efficacy endpoint does not demonstrate vaccine efficacy against genital herpes in a combined population of male and female seronegative healthy consorts of subjects with genital herpes disease.

The results of the primary efficacy endpoint analysis are summarised as follows:

1) The relative vaccine efficacy in the overall population (month 2–19 ATP) is 25.4% (95% CI:−55.5, 64.2; p=0.449). The relative vaccine efficacy for the ITT population is 37.9% (95% CI:−16.6, 67.0;p=0.143).
2) A statistically significant gender by group interaction on the efficacy analysis of the ITT population (p=0.03).
3) A separate analysis by gender shows a vaccine efficacy of 54.2% in the month 2–19 ATP female population (95% CI:−47.7, 85.8; p=0.238) and a statistically significant vaccine efficacy of 72.7% (95% CI: 19.1, 90.8; p=0.014) in the female ITT population. In the male population, there is no evidence of vaccine efficacy. In the month 2–19 ATP male population vaccine efficacy is 3.6% (95% CI:−171, 60.5) and −11.1%, (95% CI;−157.6, 52.1) in the ITT male population.

Several baseline covariates were investigated to determine whether they might influence efficacy outcomes: gender, age, frequency of condom use at baseline, frequency of sexual intercourse and duration of relationships prior to study entry. Tendency towards vaccine efficacy was associated with the female gender, age above 30 years, infrequent condom use, sexual intercourse of less than the median frequency and shorter duration of relationships. These observations applied to both ATP and ITT populations.

Secondary Efficacy Endpoint Analyses

Prevention of Genital Herpes Disease (month 7–19)

After 3 doses of the vaccine (between study months 7–19), vaccine efficacy of 81.1% (95% CI:−58.9, 97.8) was observed for prevention of genital herpes disease in females (p=0.111). No tendency toward efficacy was observed in males during the month 7–19 observation period (−2.9% vaccine efficacy, 95% CI: −624.7, 85.4; p=0.99). This tendency towards vaccine efficacy in the month 7–19 female ATP population is consistent with the observation of vaccine efficacy in females in the ITT analysis of the primary endpoint.

Prevention of HSV Infection

A comparison was made between vaccine and placebo groups for the efficacy of the vaccine in preventing HSV infection. Overall, there was no vaccine efficacy against HSV infection. However, consistent with the disease endpoint analyses, a tendency toward vaccine efficacy against HSV infection was suggested in females in the ITT population (vaccine efficacy of 46.0%, 95% CI: −2.1, 71.4; p=0.072) and in the month 7–19 ATP population (vaccine efficacy of 52.8%, 95% CI: −33.4, 83.3; p=0.184).

Time to Occurrence of Genital Herpes

Time to occurrence of genital herpes disease was calculated from study entry until the occurrence of the disease. The main analysis has been performed by the logrank test; Kaplan-Meier curves were plotted for each group. In females (month 2–19 ATP population), separation of the curves denoting the occurrence of disease cases is apparent from approximately nine months with disease cases continuing to occur in the placebo group. Vaccine efficacy is estimated at 53.6% (95% CI: −54.2, 86.0) in females. In the ITI female population where the separation of the vaccine and placebo curves is apparent from month 0, a statistically significant vaccine efficacy is estimated at 73.2% (95% CI: 18.7, 91.2; p=0.013). No vaccine efficacy is observed for the male population. Again, the results of the "time to occurrence" analysis is consistent with the primary endpoint analysis.

Severity of Genital Herpes Disease

Parameters including, duration of lesions, duration of symptoms per episode, number of symptoms per episode and intensity of symptom per episode were used to assess severity of disease in both treatment groups. In the combined month 2–19 ATP population, duration of symptoms per episode is significantly longer in the small number of cases occurring in the vaccine group (p=0.031). The gender specific severity data also reveals that in females, there is statistically significant higher number of genital herpes disease lesions per episode (p=0.010) in the vaccine group. These observations suggests that while vaccination may prevent mild to moderate disease in the vaccine group, disease with more severe manifestations were not prevented by vaccination.

EXAMPLE 3

1. Methods

The study was a multi-centre, double-blind, randomised, placebo-controlled study, based on a "modified" consort design. Study subjects (the 'exposed partners') were adults aged between 18 and 45 years of any HSV serostatus, with no history of genital herpes disease and a regular sexual partner (the 'source partner') with recurrent genital herpes disease. The source partners did not participate in the study.

HSV seronegative (HSV 1−/2−) and seropositive (HSV 1+/2−; HSV 1−/2+; HSV1+/2+) volunteers were enrolled into the study. Only subjects who were HSV-2 seronegative at entry into the study were evaluated for vaccine efficacy.

Subjects were randomly allocated into one of the following two groups, in a ratio of 1:1 (vaccine:placebo):

TABLE 1

Vaccine and placebo formulations

| Group | gD2 (mcg) | 3D-MPL (mcg) | Aluminium salt (mcg) | Volume (ml) |
|---|---|---|---|---|
| Vaccine | 20 | 50 | 500 | 0.5 |
| Placebo | — | — | 500 | 0.5 |

Subjects were vaccinated at months 0, 1, 6 and were followed for 19 months in order to detect signs or symptoms of genital HSV disease (either culture- or PCR-confirmed) and genital HSV infection (genital HSV disease or seroconversion to non-vaccinal HSV antigens). At baseline, month 7 and month 19, blood samples were taken for evaluation of anti-gG1-gG2 antibodies (ELISA) and, in a subset of subjects, anti-gD2 and neutralising anti-HSV antibodies.

In order to collect additional efficacy data and to evaluate long term safety and immunogenicity of the vaccine, an extended follow-up of an additional 24 months is being conducted with study visits at months 22, 25, 31, 37 and 43. This extended follow-up has two phases (A and B) and is still ongoing. Phase A is double-blinded and includes all time points between the end of the initial follow-up period and the date the last subject enrolled completes the month 19 visit. All placebo recipients participating in the extended follow-up are considered to have completed the study at the end of phase A. Phase B includes those subjects who have received vaccine, and ends when a total of 43 months of study participation for each individual has been completed.

2. Co-primary Objectives

Primary Safety Objective

To compare, with a placebo, the safety of SmithKline Beecham Biologicals' herpes simplex vaccine (gD-Alum-3D-MPL) in healthy adults of any HSV serostatus and whose consort has genital herpes disease.

Primary Efficacy Objective

To evaluate the protective efficacy of gD-Alum-3D-MPL vaccine to prevent acquisition of genital herpes disease in healthy female adults who are HSV seronegative (HSV 1−/2−) or HSV-1 seropositive (HSV 1+/2−) and without genital herpes disease, but whose consorts have genital herpes disease.

3. Co-primary Endpoints

Unsolicited adverse events occurring between months 0–7

Genital herpes disease in HSV 1−/2− and HSV 1+/2− females (months 0–19)

TABLE 2

Definition of genital herpes disease

HSV 1+/2− subjects:

Symptoms of genital herpes disease

Culture HSV 2 positive  OR  Seroconversion to non-vac HSV 2 Abs + positive HSV 2 PCR HSV 1−/2− subjects:

Symptoms of genital herpes disease

Culture HSV positive  OR  Seroconversion to + positive HSV PCR

4. Results

A total of 2,491 subjects (1405 men, 1086 women) were enrolled at 60 study sites (35 in US, 15 in Canada, 5 in Australia and 5 in Italy). The mean age of subjects was 33.2 years and most of the subjects were white.

TABLE 3

Demography (at screening visit)

| | |
|---|---|
| Number enrolled: | 2491 |
| Male | 56% |
| Female | 44% |
| Mean Age: | 33 years |
| Initial serostatus: | |
| HSV 1−/2− | 22% |
| HSV 1+/2− | 51% |

TABLE 3-continued

Demography (at screening visit)

| | |
|---|---|
| HSV 1−/2+ | 7% |
| HSV 1+/2+ | 14% |
| Race: | |
| White | 92% |
| Black | 3% |
| Other | 5% |

TABLE 4

Sexual history (at screening visit)

| | |
|---|---|
| Mean duration of relationship: | 37 months |
| Frequency of intercourse: | 10/month |
| Condom use: | |
| Never | 39% |
| Sometimes | 29% |
| Usually | 12% |
| Always | 19% |

One thousand, eight hundred and sixty seven (1,867) HSV-2 seronegative subjects (720 females) were analysed. The vaccine had a clinically acceptable reactogenicity profile.

The primary efficacy endpoint was not met. The gD2 vaccine provided a vaccine efficacy (months 0–19) of 42% (95% CI: −31, 74) in the combined ITT population of HSV 1−/2− and HSV 1+/2− females which was not statistically significant (P=0.18).

However, the gD2 vaccine was effective in preventing genital herpes disease in HSV 1−/2− females (VE=74%, 95% CI: 9, 93; P=0.02; ITT population). VE against genital herpes disease was not observed in males or in HSV 1+/2− females. VE against HSV infection in HSV 1−/2− females was 39% (95% CI: −6, 65, ITT population).

5. Conclusions

The primary efficacy endpoint for study 208141-017 (HSV-017) was not met. Vaccine efficacy of the gD-Alum-MPL vaccine against genital herpes disease in the combined ITT population of HSV 1−/2− and HSV 1+/2− females was not statistically significant (VE=42%, 95% CI: −31, 74; P=0.18). However, in HSV 1−/2− females, a vaccine efficacy of 74% (95% CI: 9, 93; P=0.02; ITT population) against genital herpes disease was demonstrated. These results confirm the previously observed finding of vaccine efficacy in the ITT population of HSV 1−/2− females in study 208141-005 (HSV-007), where a vaccine efficacy of 73% was observed (95% CI: 19, 91; P=0.01).

The evidence for vaccine efficacy in HSV 1−/2− males was inconclusive and there was no evidence of vaccine efficacy in HSV 1+/2− male or female subjects.

Overall Conclusions

The analysis demonstrates that while there may be a tendency toward vaccine efficacy against genital herpes, the primary endpoint analysis does not demonstrate vaccine efficacy in a combined population of male and female seronegative healthy consorts of subjects with genital herpes disease. However, a separate sub-analysis by gender group, based on observed gender interaction, surprisingly shows a tendency towards vaccine efficacy in females which is statistically significant in the ITT population. There is no evidence of vaccine efficacy in the male population.

What is claimed is:

1. A method of treating an HSV 1−/2− female human subject susceptible to herpes simplex virus (HSV) infection, which method comprises administering to the female subject in need thereof an effective amount of a vaccine formulation comprising an adjuvant and an antigen which is or is derived from the group consisting of HSV-1 glycoprotein D, HSV-2 glycoprotein D and an immunological fragment thereof.

2. The method according to claim 1 in which the adjuvant is a TH-1 inducing adjuvant.

3. The method according to claim 1 in which the HSV-2 glycoprotein D is a truncated glycoprotein.

4. The method according to claim 3 in which the truncated glycoprotein is HSV gD2 and is devoid of the C-terminal anchor region (gD2t).

5. The method according to claim 1 wherein the antigen or combination of antigens is formulated with a suitable carrier.

6. The method according to claim 5 wherein the carrier is aluminium hydroxide (alum), aluminium phosphate or an oil in water emulsion.

7. The method according to claim 6 wherein the adjuvant is the TH-1 inducing adjuvant 3D-MPL.

8. The method according to claim 7 in which the particles of 3D-MPL are small enough to be sterile filtered through a 0.22 micron membrane.

9. The method according to claim 1 wherein the vaccine formulation is used to prevent genital herpes infections.

10. The method according to claim 9 in which the vaccine formulation comprises gD2t (1–1000 μg), 3D-MPL (10–200 μg) and an aluminum salt (100–1000 μg).

11. The method according to claim 10 in which the vaccine formulation comprises gD2t (20 μg), 3D-MPL (50 μg) and alum (500 μg).

12. The method according to claim 1 wherein the vaccine formulation is administered to, or manufactured for administration to, female subjects at intervals of 0, 1 and 6 months.

13. The method according to claim 1 wherein the vaccine formulation is administered intramuscularly.

* * * * *